US011839530B2

(12) United States Patent
Lepke

(10) Patent No.: US 11,839,530 B2
(45) Date of Patent: *Dec. 12, 2023

(54) FOLDABLE ABSORBENT APPARATUS AND METHOD OF USING THE SAME

(71) Applicant: Steven Lepke, Wakefield, MA (US)

(72) Inventor: Steven Lepke, Wakefield, MA (US)

( * ) Notice: Subject to any disclaimer, the term of this patent is extended or adjusted under 35 U.S.C. 154(b) by 1302 days.

This patent is subject to a terminal disclaimer.

(21) Appl. No.: 16/145,018

(22) Filed: Sep. 27, 2018

(65) Prior Publication Data
US 2019/0192355 A1    Jun. 27, 2019

Related U.S. Application Data

(63) Continuation of application No. 14/744,880, filed on Jun. 19, 2015, now Pat. No. 10,123,912.

(51) Int. Cl.
*A61F 13/12* (2006.01)
*A61F 13/45* (2006.01)
*A61F 13/20* (2006.01)
*A61F 13/00* (2006.01)

(52) U.S. Cl.
CPC .......... *A61F 13/2008* (2013.01); *A61F 13/12* (2013.01); *A61F 13/45* (2013.01); *A61F 2013/00174* (2013.01); *A61F 2013/00285* (2013.01); *A61F 2013/4512* (2013.01)

(58) Field of Classification Search
CPC ...... A61F 13/12; A61F 13/2008; A61F 13/45; A61F 2013/00174; A61F 2013/00285; A61F 2013/4512; A61F 13/2005
See application file for complete search history.

(56) References Cited

U.S. PATENT DOCUMENTS

| | | | | | |
|---|---|---|---|---|---|
| 1,971,606 | A | * | 8/1934 | Grant | A61F 13/514 604/386 |
| 2,076,526 | A | * | 4/1937 | Brown | A61F 13/2008 604/375 |
| 3,468,030 | A | * | 9/1969 | Nivison | A61F 13/2022 433/136 |
| 4,705,514 | A | * | 11/1987 | Barnard | A61F 13/2051 433/136 |
| 4,765,323 | A | * | 8/1988 | Poettgen | B32B 27/32 128/849 |
| 4,901,738 | A | * | 2/1990 | Brink | B32B 15/14 606/2 |
| 4,936,319 | A | * | 6/1990 | Neubardt | A61B 46/00 128/849 |
| 5,071,349 | A | * | 12/1991 | Skinner | A61C 5/90 433/136 |
| 5,135,792 | A | * | 8/1992 | Hogan | A61B 16/00 428/68 |

(Continued)

*Primary Examiner* — Bradley H Philips
(74) *Attorney, Agent, or Firm* — Law Office of Jerry Joseph, PLC; Jerry Joseph

(57) ABSTRACT

A foldable absorbent apparatus to ameliorate bleeding of a wound which includes a first and second absorbent pad layer to absorb a fluid, and a malleable material layer enclosed within the first and second absorbent layer configured to be formed in various shapes, wherein the malleable material allows the first and second absorbent pad layers to be formed in various shapes to apply a pressure to a wound while at the same time absorbing fluids from the wound to promote healing of the wound.

9 Claims, 12 Drawing Sheets

(56) References Cited

U.S. PATENT DOCUMENTS

| | | | | |
|---|---|---|---|---|
| 5,749,729 | A * | 5/1998 | Skinner | A61F 13/2074 433/136 |
| 6,824,853 | B1 * | 11/2004 | Levine | A61B 46/40 405/60 |
| 2005/0137562 | A1 * | 6/2005 | Mizutani | A61F 13/47209 604/385.17 |
| 2006/0089584 | A1 * | 4/2006 | McAdams | A61F 13/2051 433/136 |
| 2006/0142718 | A1 * | 6/2006 | Maass | A61F 13/12 604/370 |
| 2012/0330253 | A1 * | 12/2012 | Robinson | A61F 13/025 604/319 |

* cited by examiner

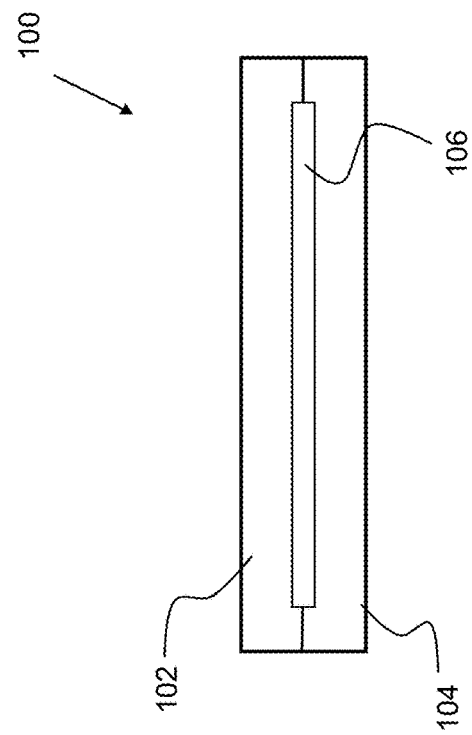
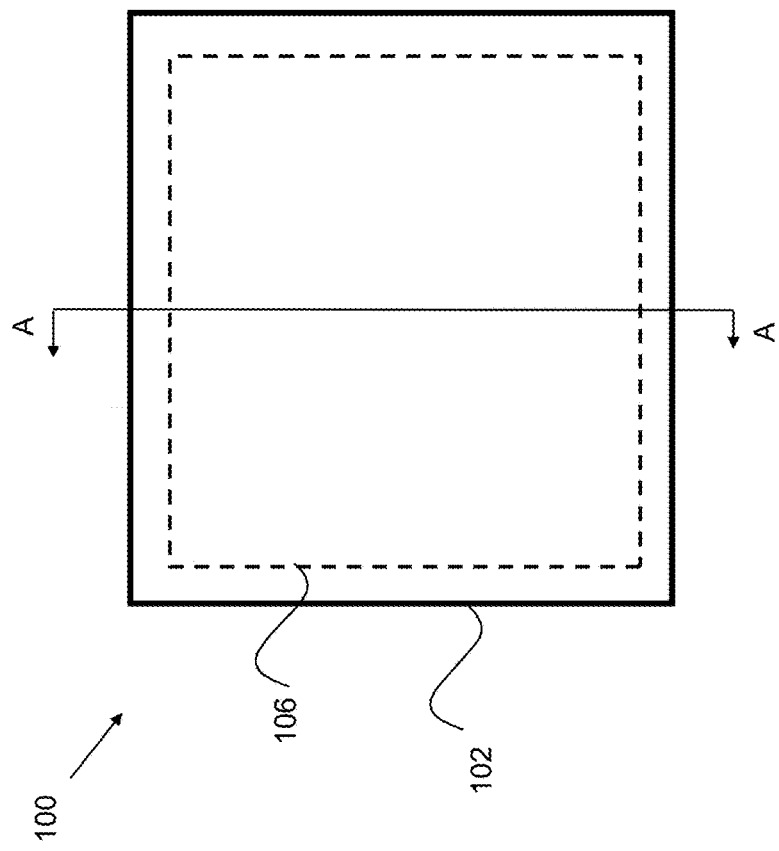
FIG. 4B
FIG. 4A

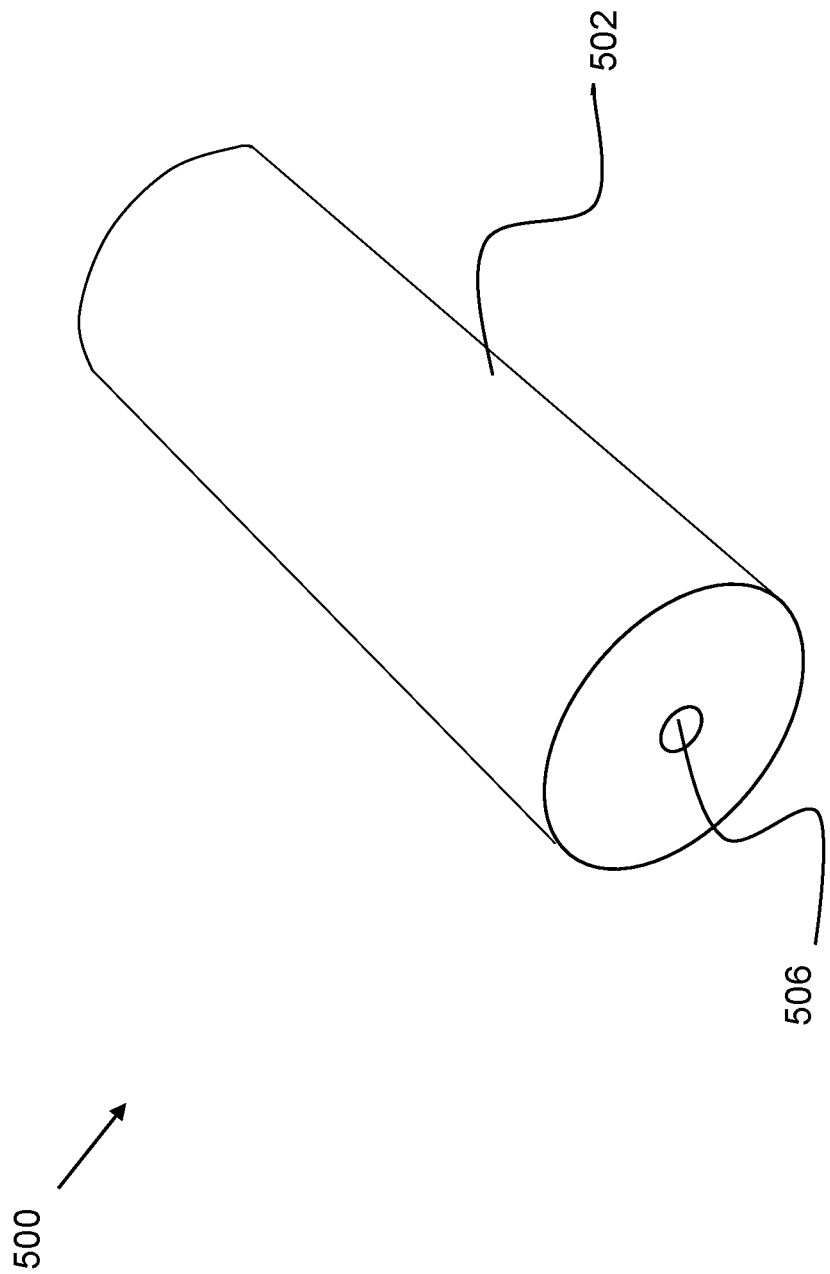

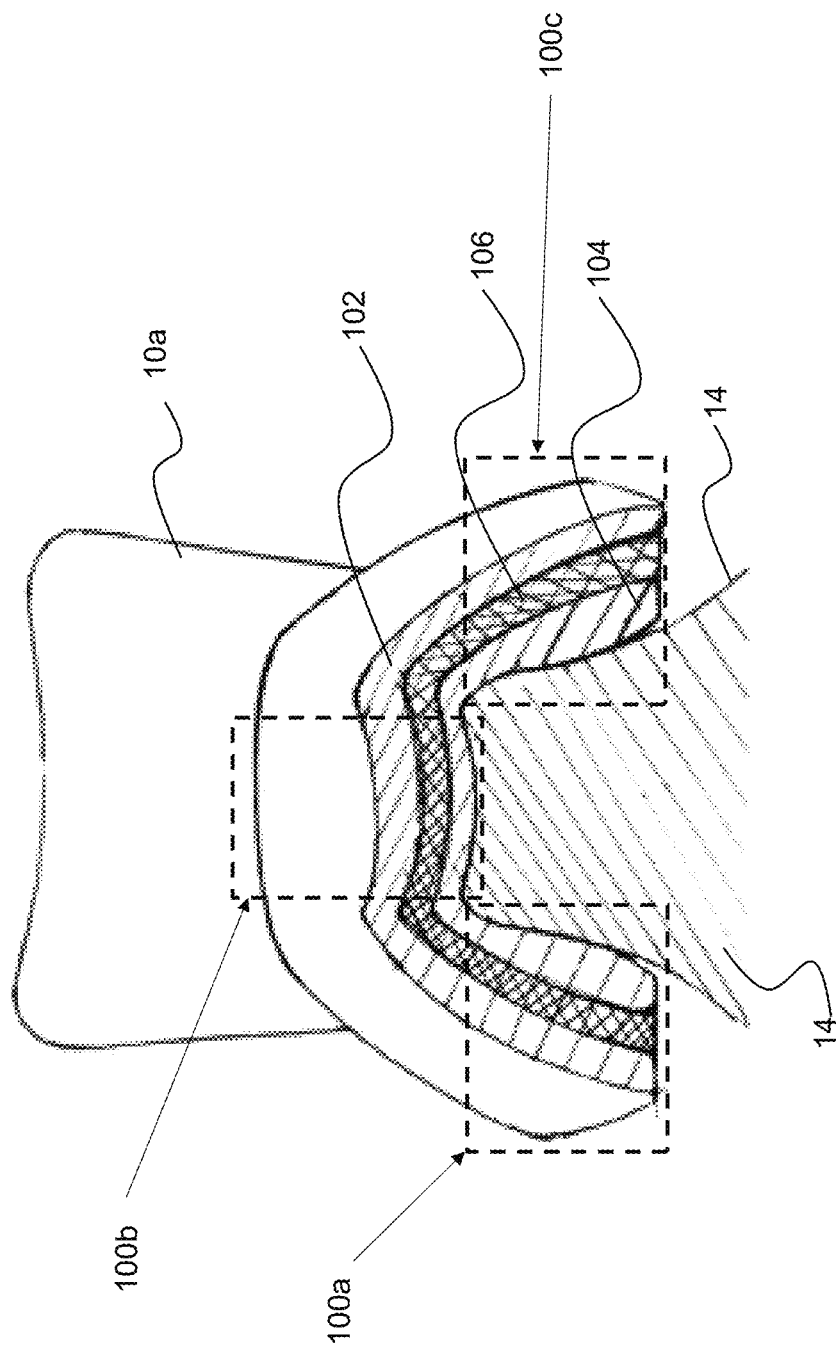

FOLDABLE ABSORBENT APPARATUS AND METHOD OF USING THE SAME

CROSS-REFERENCE TO RELATED APPLICATIONS

This application claims the benefit of U.S. Provisional Patent Application No. 62/015,411, filed on Jun. 21, 2014, the disclosure of which is incorporated herein in its entirety by reference.

BACKGROUND OF THE INVENTION

1. Field of Invention

This invention pertains to a foldable absorbent pad, and more particularly to a foldable absorbent apparatus designed to apply and maintain a constant pressure to a wound or tooth socket to ameliorate bleeding and to promote healing.

2. Description of the Related Art

FIG. 1 illustrates a user's lower set of teeth 10. As illustrated in FIG. 1, the user has a lower set of teeth 10 having an empty tooth socket 12 where a tooth had been previously extracted. Each tooth 10a is disposed and secured within the user's gums 14 and jaw bone 16. Tooth extractions are performed for a variety of reasons including tooth decay, periodontal disease, or dental trauma. In some cases, teeth 10a are extracted merely to provide space so that the remaining teeth 10a may be straightened.

However, when a tooth 10a is extracted, the exposed tooth socket 12 bleeds continuously for a period of time which puts the user at risk for excessive blood loss and infection. As a result, the user or a medical professional must apply and maintain a constant amount of pressure to the exposed tooth socket 12 for a certain period of time in order to promote clotting to stop the bleeding. However, if a constant amount of pressure is not properly applied, the bleeding may continue, thereby risking the health and well-being of the user.

Conventionally, a piece of gauze or the like is rolled up and forced into the tooth socket 12 and held down by the medical professional to apply constant pressure to the wound. In addition, the user may be required to apply pressure by biting down on the gauze, however, if the user talks or readjusts his teeth 10a, this would reduce the amount of pressure applied to the tooth socket 12, thereby potentially dislodging the blood clot and restarting the bleeding within tooth socket 12. In order to reduce risk to the user, conventional solutions require a medical professional or user (i.e., patient) to manually hold the gauze in place, which often takes a considerable amount of time, and therefore expense.

Thus, what is desired is a foldable absorbent apparatus capable of applying a constant pressure to a wound or tooth socket, without assistance, while at the same time absorbing fluids from the wound to ameliorate bleeding and to promote healing.

BRIEF SUMMARY OF THE INVENTION

According to one embodiment of the present general inventive concept, a formable or foldable absorbent apparatus that can apply and maintain a constant pressure to a desired wound or tooth socket by retaining its formed shape is provided.

Another embodiment of the present general inventive concept provides dental and surgical absorbent pads having a malleable material disposed therein to allow the absorbent pad to be foldable into a desired shape in order to apply and maintain a constant pressure to a wound while at the same time absorbing blood and/or other fluids from the wound to ameliorate bleeding and to promote healing.

Another embodiment of the present general inventive concept provides a foldable absorbent apparatus formed in various shapes including rectangular, circular, and cylindrical having an anti-microbial coating and designed to be formed to apply a constant pressure to a wound while at the same time absorbing blood and/or other fluids from the wound to ameliorate bleeding and to promote healing.

Another embodiment of the present general inventive concept provides a foldable absorbent cylindrical apparatus having an anti-microbial coating designed to be formed in various shapes required to apply a constant pressure to a wound while at the same time absorbing blood and/or other fluids from the wound to ameliorate bleeding and to promote healing.

Another embodiment of the present general inventive concept provides a foldable absorbent apparatus designed to be detected by imaging devices such as x-ray, CT scan, infra-red, and the like so that the foldable absorbent apparatus may be easily located and removed after surgical procedures. In alterative exemplary embodiments, the foldable absorbent apparatus may include a magnetic malleable material so that the foldable absorbent apparatus can be easily located and removed when used in medical, surgical, and/or veterinary procedures.

In accordance with the various features of the present general inventive concept there is provided a foldable absorbent apparatus to ameliorate bleeding of a wound which includes a first and second absorbent pad layer to absorb a fluid, and a malleable material layer enclosed or disposed within the first and second absorbent layer and configured to be formed in various shapes, wherein the malleable material allows the first and second absorbent pad layers to be formed into the various shapes to apply and maintain a constant pressure to a wound while at the same time absorbing fluids from the wound to ameliorate bleeding and to promote healing of the wound.

The foldable absorbent apparatus may further include a medication coating layer disposed between the first and second absorbent layers.

The foldable absorbent apparatus may further include a time-release layer disposed between the first absorbent layer and the medication layer to control a time the medication coating layer reaches the first absorbent layer.

The medication coating layer may include at least one of a pain medication, a coagulant, an antibiotic, and an antibacterial agent.

The first and second absorbent layer may be formed of at least one material selected from a group consisting of cotton, gauze, and a polymer material.

The polymer material may be formed of at least one material selected from a group consisting of polyacrylate, chitosan, polyamine, polylysine, polyethylene, xanthan, a cellulosic polymer, a dextran, a starch, or any combinations thereof.

The foldable absorbent apparatus may further include a friction member disposed on an outer surface of at least one of the first absorbent layer and the second absorbent layer to help hold on to a user's gums or jaw bone.

In accordance with the various features of the present general inventive concept there is also provided a cylindrical foldable absorbent apparatus to ameliorate bleeding of a wound which includes a cylindrical absorbent pad layer to absorb a fluid, and a wire shaped malleable material layer enclosed within the cylindrical absorbent layer configured to be formed in various shapes, wherein the malleable material allows the cylindrical absorbent pad layers to be formed in various shapes to apply a constant pressure to a wound while at the same time absorbing fluids from the wound to promote healing of the wound.

The cylindrical foldable absorbent apparatus may further include a medication coating layer disposed within the cylindrical absorbent pad layer.

The cylindrical foldable absorbent apparatus may further include a time-release layer disposed between the cylindrical absorbent pad layer and the medication layer to control a time the medication coating layer reaches the cylindrical absorbent pad layer.

The medication coating layer may include at least one of a pain medication, a coagulant, an antibiotic, and an antibacterial agent.

The cylindrical foldable absorbent apparatus may further include a friction member disposed on an outer surface of the cylindrical absorbent pad layer to maintain a position on the wound.

The cylindrical absorbent pad layer may be formed of at least one material selected from a group consisting of cotton, gauze, and a polymer material.

In accordance with the various features of the present general inventive concept there is also provided a method of ameliorating bleeding of a wound using a foldable absorbent apparatus having a first and second absorbent pad layer to absorb a fluid and a malleable material layer enclosed within the first and second absorbent layer configured to be formed in various shapes, wherein the malleable material allows the first and second absorbent pad layers to be formed in various shapes to apply a pressure to a wound while at the same time absorbing fluids from the wound to promote healing of the wound, the method includes obtaining a foldable absorbent apparatus to be used on a wound, forming the foldable absorbent apparatus to surround the wound, wherein the foldable absorbent apparatus is folded so that a first portion of the is pressed against the wound by pressure maintained by a second portion of the foldable absorbent apparatus, and applying a force onto the formed foldable absorbent apparatus to secure the second portion against a portion surrounding the wound to maintain a constant pressure of the first portion on the wound.

The method may include rolling the foldable absorbent apparatus such that a width of the first portion corresponds to a width of the wound.

The method may further include placing the formed foldable absorbent apparatus to cover the wound and pressing the second portion against areas surrounding the wound for support.

BRIEF DESCRIPTION OF THE SEVERAL VIEWS OF THE DRAWINGS

The above-mentioned features of the invention will become more clearly understood from the following detailed description of the invention read together with the drawings in which:

FIG. 4A is a top plan view of the foldable absorbent apparatus illustrated in FIG. 2;

FIG. 4B is a cross-sectional view of the foldable absorbent apparatus illustrated in FIG. 4A, along line A-A;

FIG. 8A is a top perspective view of a foldable absorbent apparatus according to another exemplary embodiment of the present general inventive concept;

FIG. 9C illustrates a detailed cross-sectional view of the foldable absorbent apparatus in FIG. 9A pressed into the exposed tooth socket, wherein portions of the foldable absorbent apparatus are pressed against gums surrounding the tooth socket to apply and maintain constant pressure.

DETAILED DESCRIPTION OF THE INVENTION

An exemplary embodiment of the present general inventive concept provides a foldable absorbent apparatus that simultaneously provides unassisted constant pressure and fluid absorption of a wound within a user's mouth in order to ameliorate bleeding and to promote healing. However, the present general inventive concept is not limited thereto. That is, in alternative exemplary embodiments, the foldable absorbent apparatus may be designed for a plurality of medical issues requiring both fluid absorption and constant pressure, such as nose bleeds, gunshot wounds, surgical procedures, veterinary procedures, and the like.

Another exemplary embodiment of the present general inventive concept provides a method of using a foldable absorbent apparatus that provides unassisted constant pressure and fluid absorption to a wound in order to ameliorate bleeding and promote healing.

The foldable absorbent apparatus according to the present general inventive concept includes various types of malleable material disposed between various types of absorbent material to ameliorate bleeding and to promote healing of tooth sockets after dental procedures by applying and maintaining a constant amount of pressure on the tooth socket or other wound, without external assistance from the user or medical professional.

Those skilled in the art will recognize that the utility of having an integrated foldable absorbent apparatus which provides both constant pressure to a wound (i.e. tooth socket) while at the same time absorbing blood and other fluids from the wound as disclosed by present general inventive concept may be performed with various sized and shaped malleable materials covered with corresponding sized and shaped absorbent pads, such as gauze. That is, the foldable absorbent apparatus of the present invention may be formed in various shapes, sizes, and configurations which can be used in various applications without departing from the spirit and scope of the present general inventive concept.

Figure 1:
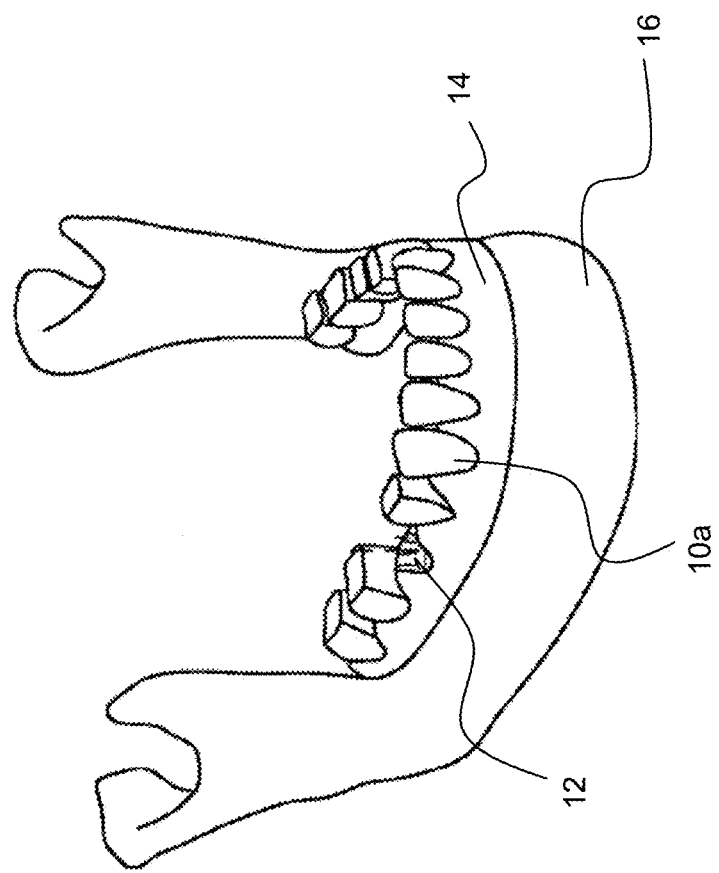
FIG. 1 is a perspective view of a user's lower set of teeth, gums, and jaw bone.
Figure 2:
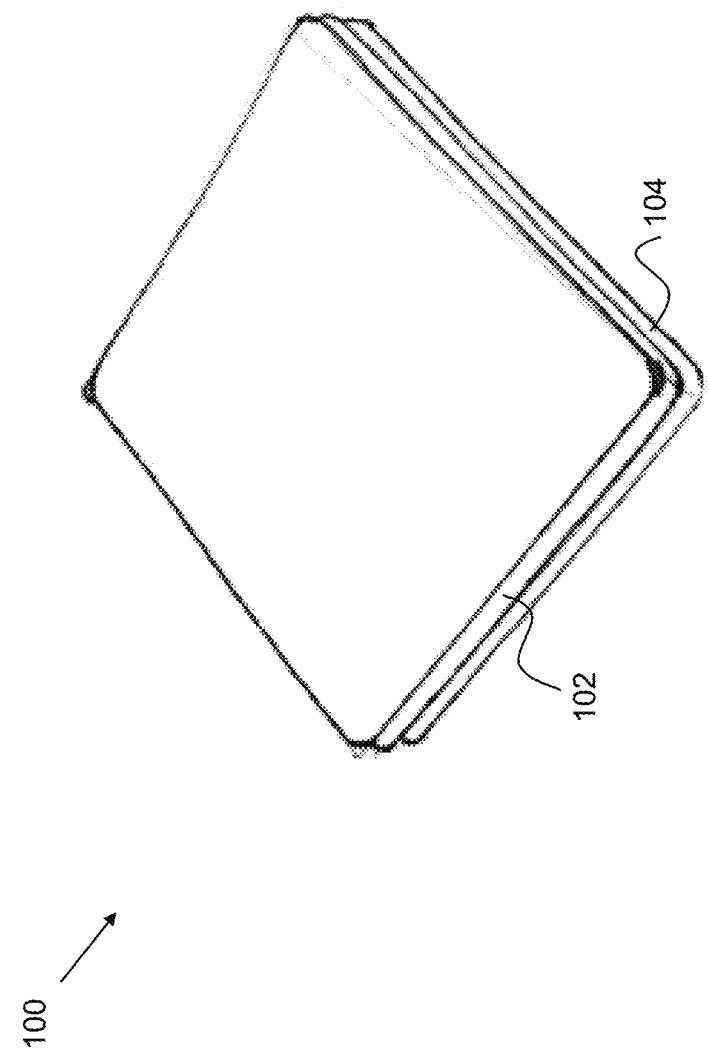
FIG. 2 is a top perspective view of a foldable absorbent apparatus according to an exemplary embodiment of the present general inventive concept.
Figure 3:
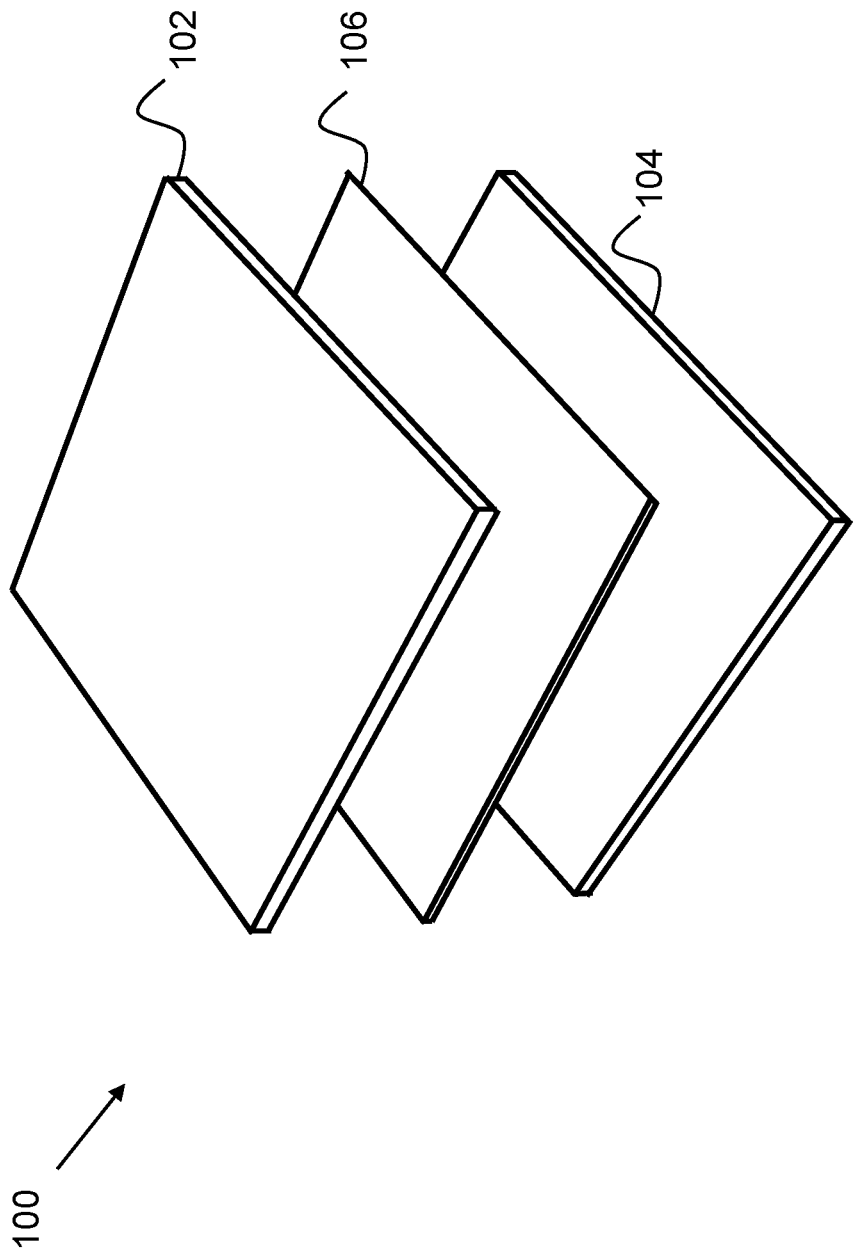
FIG. 3 is an exploded top perspective assembly view of the foldable absorbent apparatus illustrated in FIG. 2.

FIG. 2 is a top perspective view of a foldable absorbent apparatus 100 according to an exemplary embodiment of the present general inventive concept. FIG. 3 is an exploded top perspective assembly view of the foldable absorbent apparatus 100 illustrated in FIG. 2.

Referring to FIGS. 2 and 3, a foldable absorbent apparatus 100 according to an exemplary embodiment of the present general inventive concept includes a first absorbent pad layer 102, a second absorbent pad layer 104, and a malleable material layer 106 disposed between (or enclosed within) the first and second absorbent pad layers 102, 104. The first and second absorbent pad layers 102 and 104 may be formed of various wound dressing and/or absorbent materials, such as gauze or the like. However, the present general inventive concept is not limited thereto. That is, in alternative exemplary embodiments, the first and second absorbent pad layers 102 and 104 may be formed as a matrix of a cotton or a polymer form material, such as polyacrylate, chitosan, polyamine, polylysine, polyethylene, xanthan, a cellulosic polymer, a dextran, a starch, or any combinations thereof.

In the present exemplary embodiment, the malleable member 106 may include a metal, a polymer, an alloy, a fiber, foil, or any other material which is malleable or formable to various shapes and is capable of retaining the shape in order to secure and hold the foldable absorbent apparatus 100 in a desired position or shape. In exemplary embodiments, the malleable member 106 may be biocompatible with humans and/or animals. However, the present general inventive concept is not limited thereto.

In the present exemplary embodiment, the malleable member 106 is formed in a planar sheet or foil and disposed within a top (i.e., a first) absorbent pad layer 102 and a bottom (i.e., a second) absorbent pad layer 104. The malleable material 106 allows the first and second absorbent pad layers 102 and 104 to be formed in various shapes in order to apply a constant pressure to a wound of a user, while at the same time absorbing fluids from the wound to promote healing of the wound. In exemplary embodiments, the malleable member 106 is completely enclosed by the first and second absorbent pad layers 102, 104. However the present general inventive concept is not limited thereto. That is, in alternative exemplary embodiments, the first and second absorbent pad layers 102, 104 may be disposed on a portion of or on the entire malleable member 116. In exemplary embodiments, the first and second absorbent pad layers 102, 104 may be formed from a single piece of material folded to surround the malleable material layer 106 (e.g., a malleable foil).

FIG. 4A is a top plan view of the foldable absorbent apparatus illustrated in FIG. 2. FIG. 4B is a cross-sectional view of the foldable absorbent apparatus illustrated in FIG. 4A, along line A-A. Referring to FIG. 4A, the malleable material 106 may be completely surrounded by a border created by the first and second absorbent pad layers 102, 104. The malleable material 106 may be disposed in a central portion of the assembly of the first and second absorbent pad layers 102, 104.

Figure 5B:
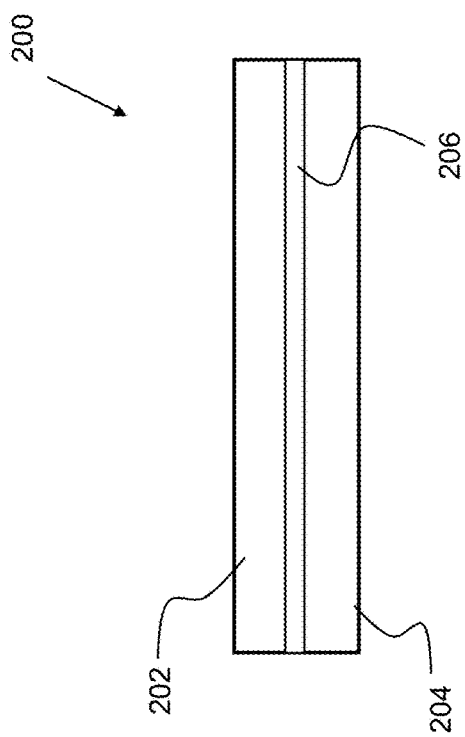
FIG. 5B is a cross-sectional view of the foldable absorbent apparatus illustrated in FIG. 5A, along line B-B.
Figure 5A:
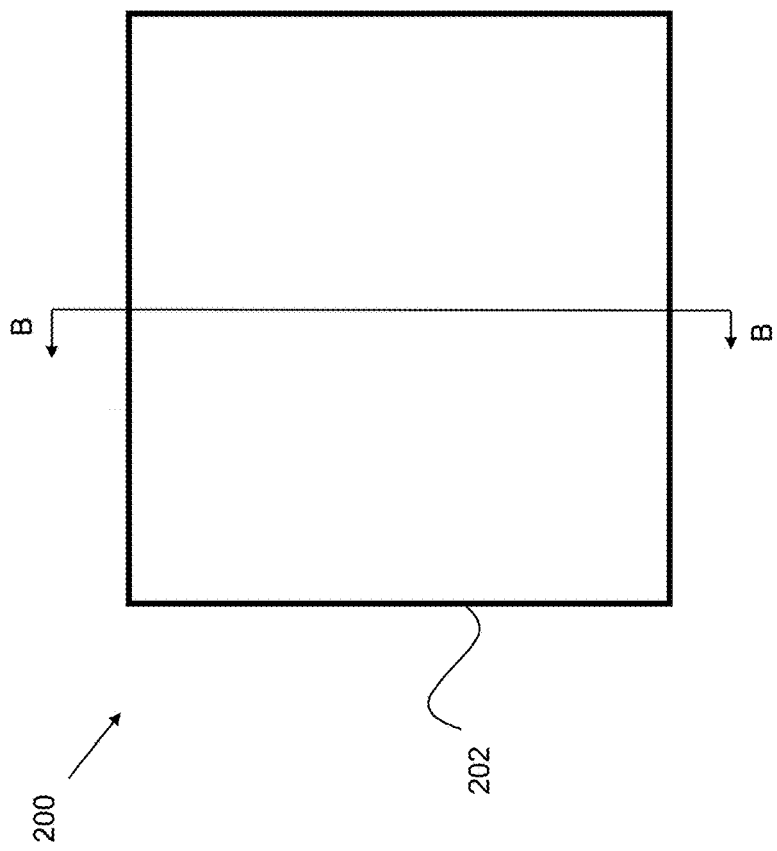
FIG. 5A is a top plan view of a foldable absorbent apparatus according to another exemplary embodiment of the present general inventive concept.

FIG. 5A is a top plan view of a foldable absorbent apparatus 200 according to another exemplary embodiment of the present general inventive concept. FIG. 5B is a cross-sectional view of the foldable absorbent apparatus 200 illustrated in FIG. 5A, along line B-B.

Referring to FIG. 5A and 5B, the foldable absorbent apparatus 200 is similar to the embodiment described above however, the malleable material 206 extends to edges of the first and second absorbent layers 202 and 204.

Figure 6B:
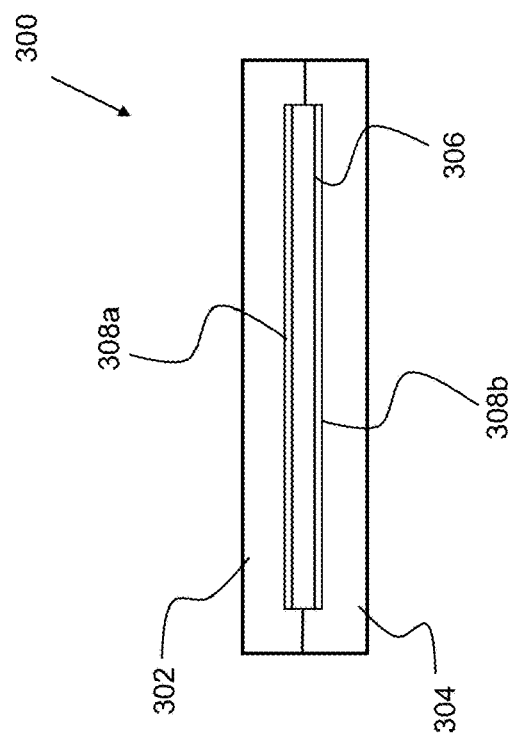
FIG. 6B is a cross-sectional view of the foldable absorbent apparatus illustrated in FIG. 6A, along line C-C.
Figure 6A:
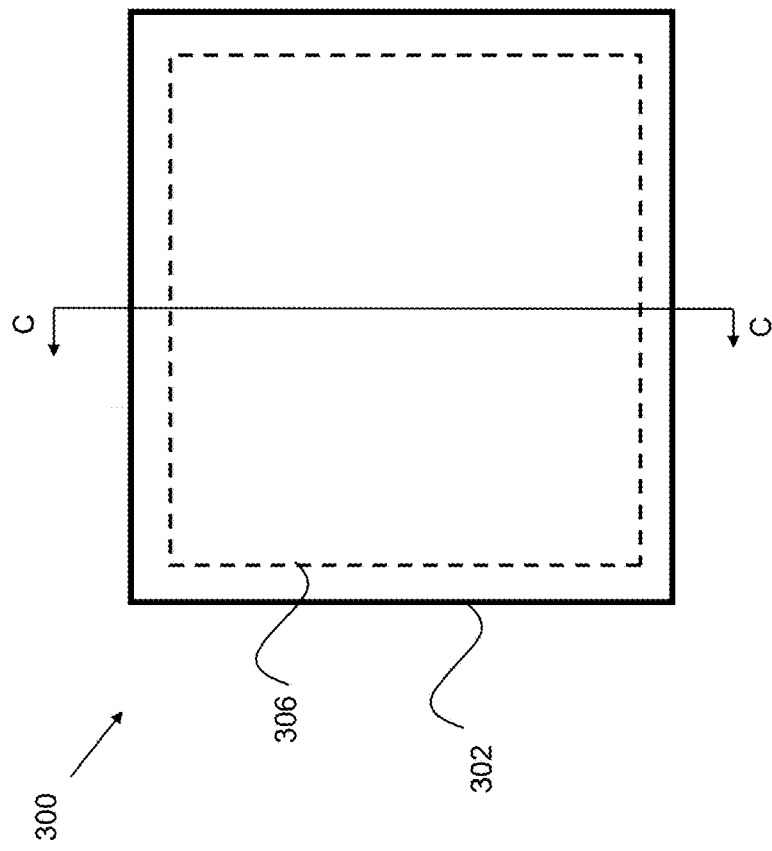
FIG. 6A is a top plan view of a foldable absorbent apparatus according to another exemplary embodiment of the present general inventive concept.

FIG. 6A is a top plan view of a foldable absorbent apparatus 300 according to another exemplary embodiment of the present general inventive concept. FIG. 6B is a cross-sectional view of the foldable absorbent apparatus 300 illustrated in FIG. 6A, along line C-C.

Referring to FIG. 6A and 6B, the foldable absorbent apparatus 300 is similar to the embodiment described above in FIG. 4A and further includes a first medication coating 308a disposed between the first absorbent layer 302 and the malleable material 306, and a second medication coating 308b disposed between the second absorbent layer 304 and the malleable material 306. In exemplary embodiments, the medication coating layers 308 includes at least one of a pain medication, a coagulant, an antibiotic, and an anti-bacterial agent. However, the present general inventive concept is not limited thereto.

Figure 7B:
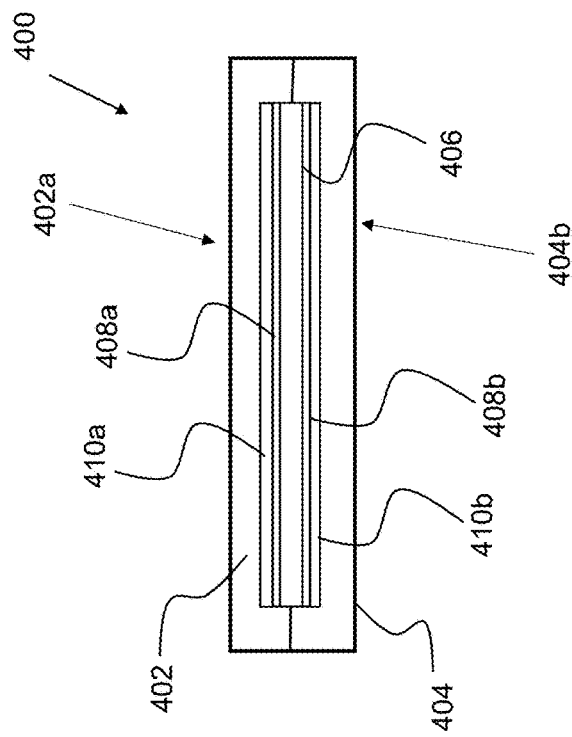
FIG. 7B is a cross-sectional view of the foldable absorbent apparatus illustrated in FIG. 7A, along line D-D.
Figure 7A:
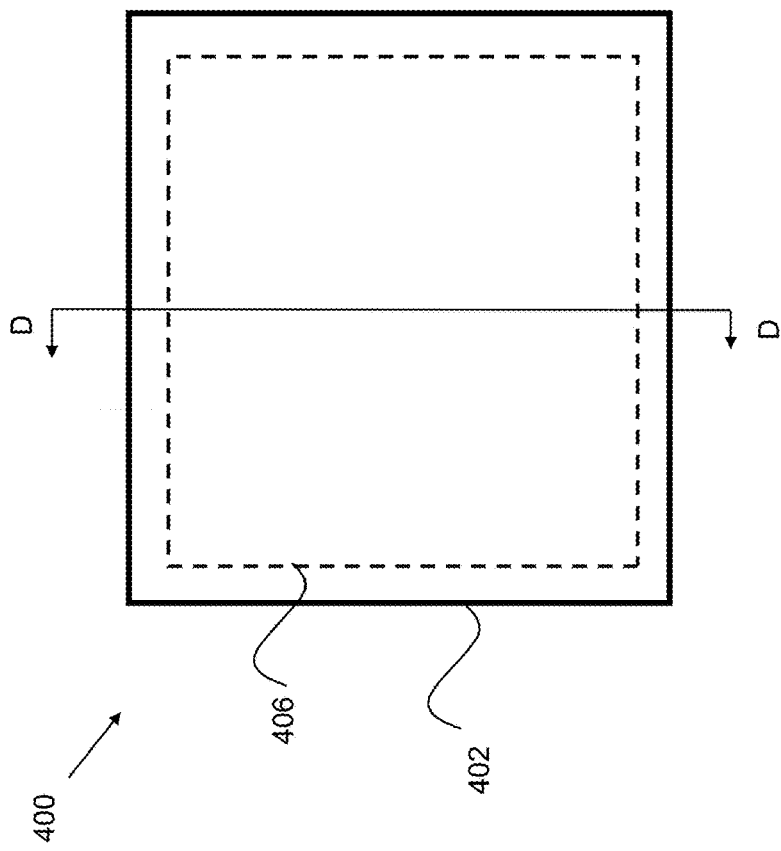
FIG. 7A is a top perspective view of a foldable absorbent apparatus according to another exemplary embodiment of the present general inventive concept.

FIG. 7A is a top perspective view of a foldable absorbent apparatus 400 according to another exemplary embodiment of the present general inventive concept. FIG. 7B is a cross-sectional view of the foldable absorbent apparatus 400 illustrated in FIG. 7A, along line D-D.

Referring to FIG. 7A and 7B, the foldable absorbent apparatus 400 is similar to the embodiments described above and further includes a first time release layer 410a disposed between the first absorbent layer 402 and the first medication coating layer 408a, and a second time release layer 410b disposed between the second absorbent layer 404 and the second medication coating layer 408b. The first and second time-release layers 410a, 410b are designed to control an amount and rate of medication within the medication coating layer 408 that reaches an outer surface 402a, 404a of the absorbent pad layer and absorbed within the wound of the user. That is, the time release layer 410a, 410b may be specifically designed so as to allow a desired dose of the medication to be delivered to the user over a desired period of time. In exemplary embodiments, the medication coating layer 408a, 408b includes at least one of a pain medication, a coagulant, an antibiotic, and an anti-bacterial agent. However, the present general inventive concept is not limited thereto.

In alternative exemplary embodiments, the foldable absorbent apparatus may further include a friction member (not illustrated) disposed on an outer surface 402a, 404a of at least one of the first and second absorbent layers 402 and 404 to help hold the foldable absorbent apparatus against a user's gums. The friction member would help the foldable absorbent apparatus hold on to an area surrounding a wound or tooth socket, such as a user's gums or jaw, to thereby provide and maintain a desired force onto the wound or tooth socket.

Figure 8B:
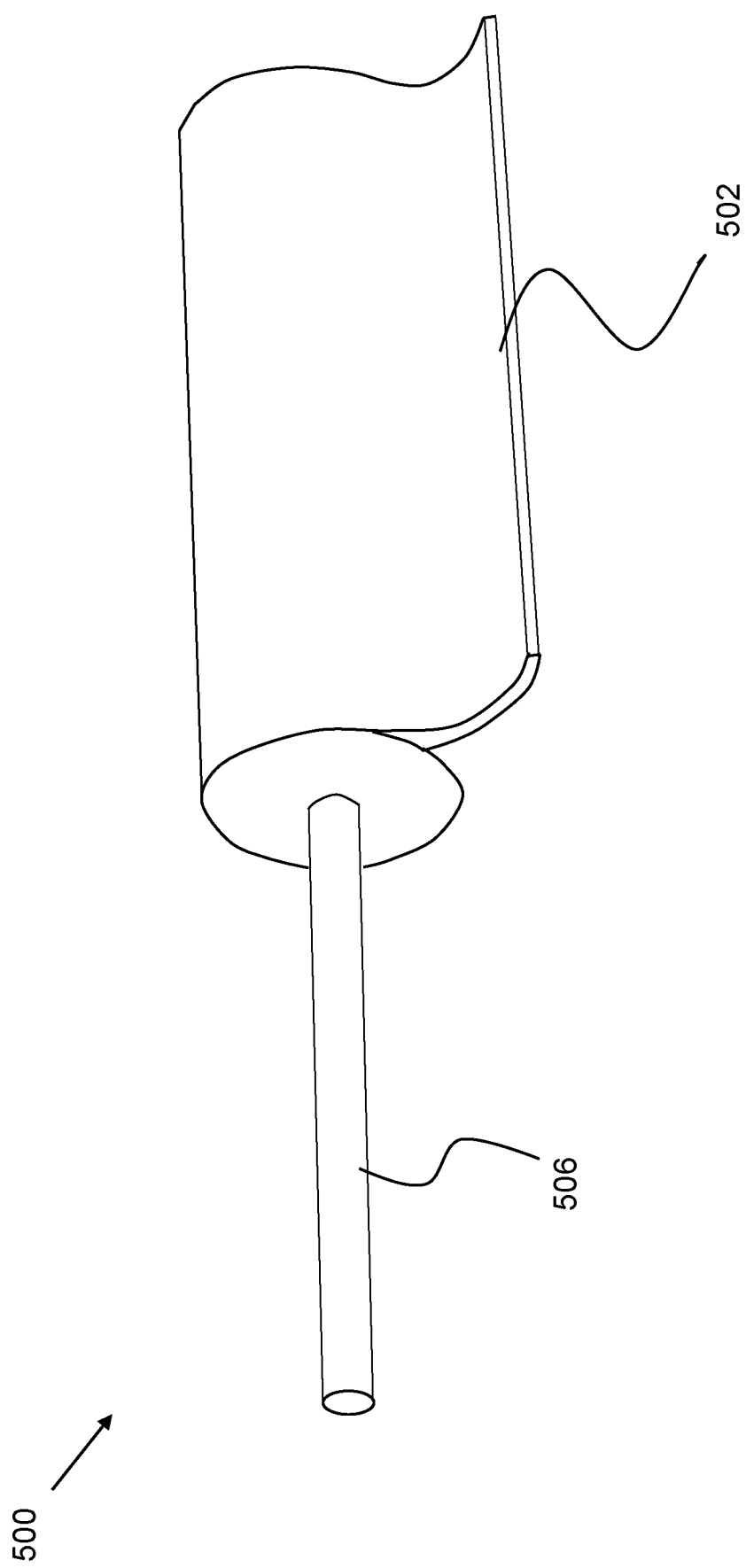
FIG. 8B is a partially exploded perspective assembly view of the foldable absorbent apparatus illustrated in FIG. 8A.

FIG. 8A is a top perspective view of a foldable absorbent apparatus 500 according to another exemplary embodiment of the present general inventive concept. FIG. 8B is a partially exploded perspective assembly view of the foldable absorbent apparatus 500 illustrated in FIG. 8A.

Referring to FIG. 8A and 8B, the foldable absorbent apparatus 500 according to the present exemplary embodiment in formed in a cylindrical or tubular shape. That is, the absorbent pad layer 502 is formed in a cylindrical or tubular shape and a wire shaped malleable material 506 is disposed therein. The absorbent pad layer 502 and the malleable material 506 are substantially similar to the absorbent pad layers and malleable materials 506 disclosed above. The cylindrically absorbent pad layer 502 is designed to absorb a fluid including blood and/or other bodily fluids during dental, medical, or veterinary procedures. However, the present general inventive concept is not limited thereto. The malleable material layer 506 may be enclosed within the cylindrical absorbent layer 506 and is configured to be formed in various shapes in order to apply a pressure to a wound while at the same time absorbing fluids from the wound to promote healing of the wound.

Figure 8D:
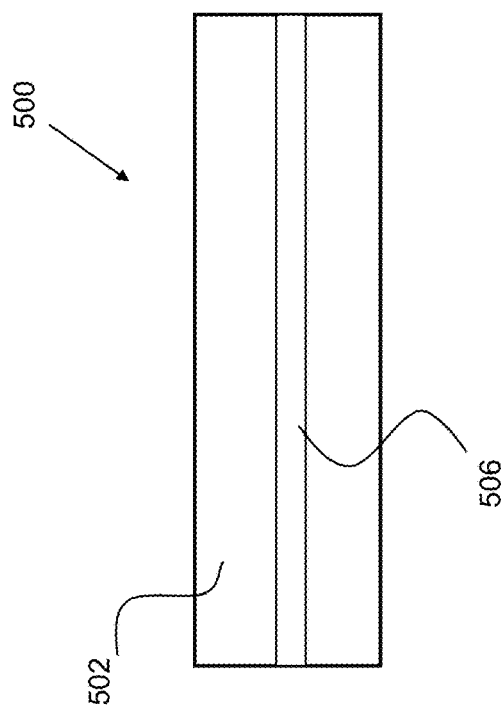
FIG. 8D is a cross-sectional view of the foldable absorbent apparatus illustrated in FIG. 8C, along line E-E.
Figure 8C:
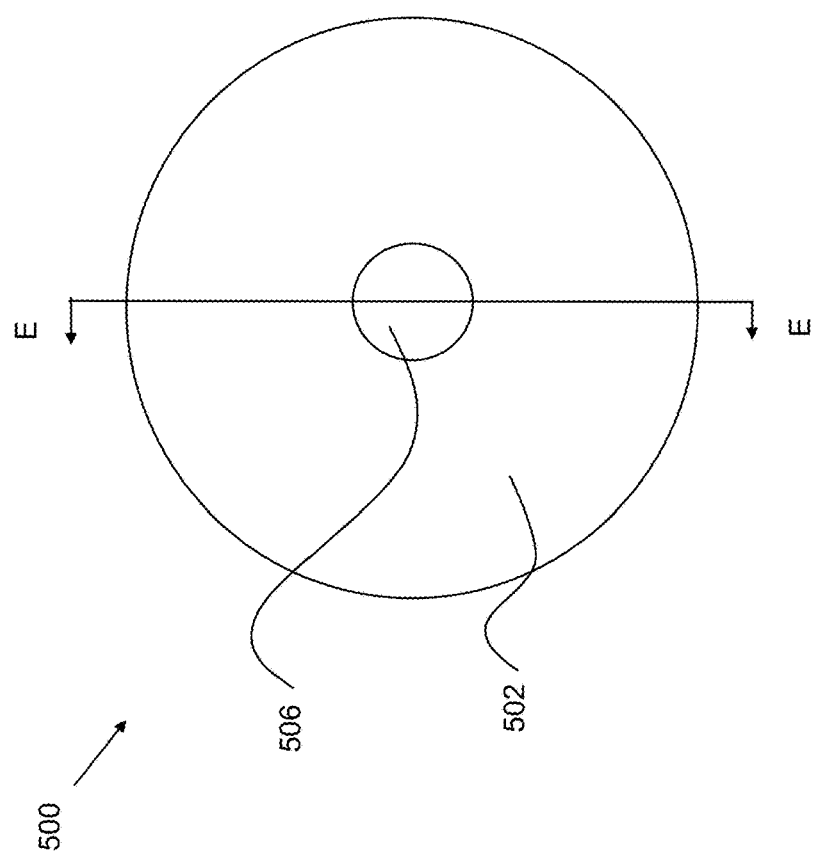
FIG. 8C is a front plan view of the foldable absorbent apparatus illustrated in FIG. 8A.

FIG. 8C is a front plan view of the foldable absorbent apparatus illustrated 500 in FIG. 8A. FIG. 8D is a cross-sectional view of the foldable absorbent apparatus 500 illustrated in FIG. 8C, along line E-E. As illustrated, in FIG. 8C and 8D, the wire or tube shaped malleable materials 506 may be disposed within a central portion of the cylindrically shaped absorbent pad layer 502. However, the present general inventive concept is not limited thereto.

Figure 9B:
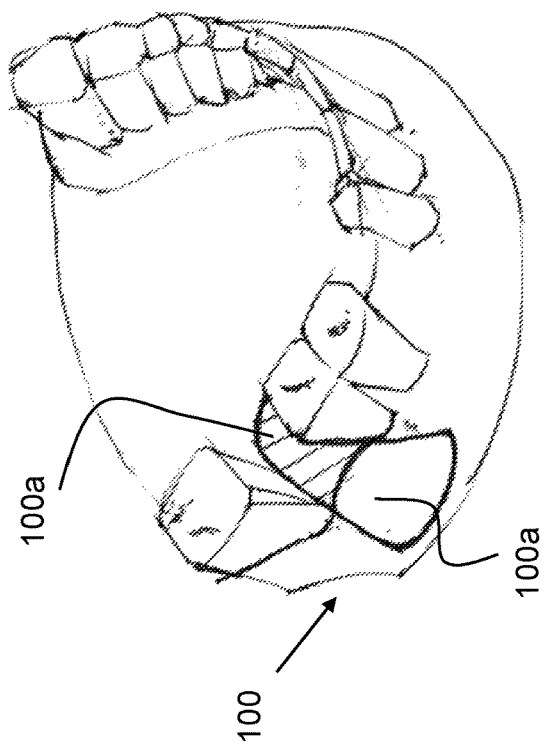
FIG. 9B illustrates the foldable absorbent apparatus in FIG. 9A in a rolled up state, engaged with the exposed tooth socket.
Figure 9A:
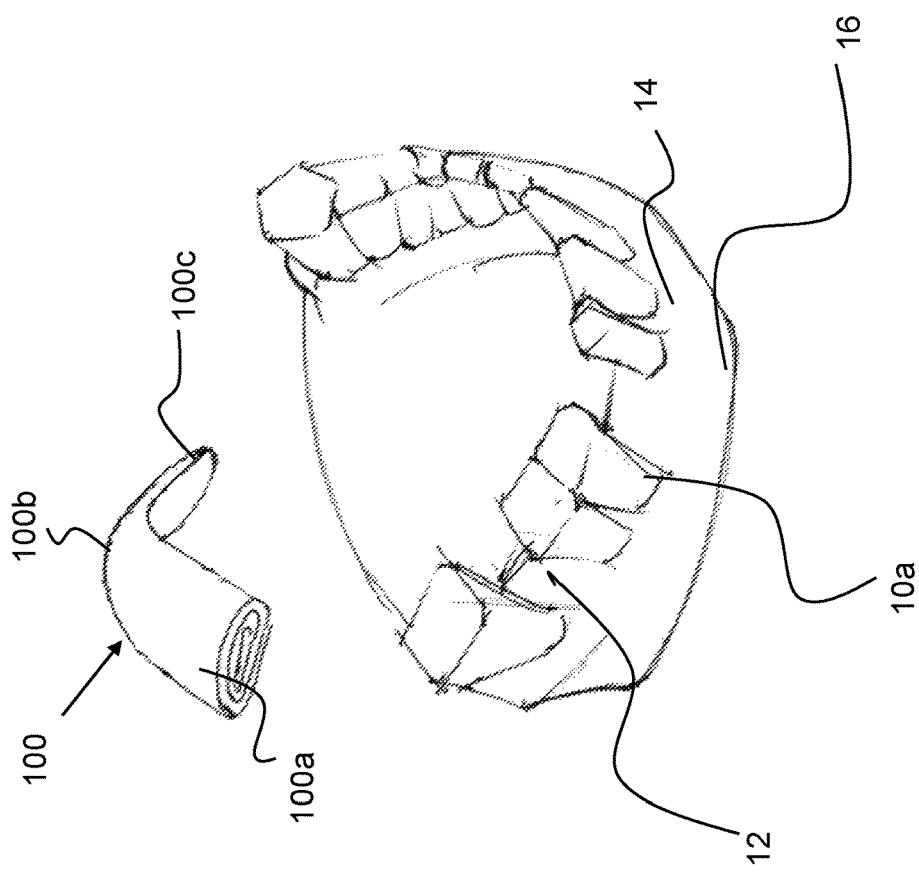
FIG. 9A illustrates an exploded view of the foldable absorbent apparatus illustrated in FIG. 2 in a rolled-up state, engaging an exposed tooth socket.

FIG. 9A illustrates an exploded view of the foldable absorbent apparatus illustrated in FIG. 2 in a rolled-up state, engaging an exposed tooth socket. FIG. 9B illustrates the foldable absorbent apparatus in FIG. 9A in a rolled up state, engaged with the exposed tooth socket and FIG. 9C illustrates a detailed cross-sectional view of the foldable absorbent apparatus in FIG. 9A pressed into the exposed tooth socket, wherein portions of the foldable absorbent apparatus are pressed against gums surrounding the tooth socket to apply and maintain a constant pressure.

FIGS. 9A-92 illustrate an exemplary method 600 of using the foldable absorbent apparatus 100 to ameliorate bleeding of a tooth socket 12 according to the present general inventive concept. There a variety of issues which necessitates extraction of a tooth 10a from a tooth socket. For example, tooth decay caused by bacteria, overcrowding within a user's mouth, or for aesthetic orthodontic treatment. However, during and after tooth extraction procedures, the tooth socket often bleeds for a significant period of time. As a result, the user or a medical professional must apply a constant amount of pressure to the exposed wound (i.e. tooth socket) for a certain period of time in order to promote clotting to stop the bleed, and to promote healing.

Referring to FIG. 9A, in the present exemplary embodiment, a foldable absorbent apparatus 100 having a length dimension and width dimension larger than a size of the tooth socket 12 or other wound is obtained. A user may then roll the foldable absorbent apparatus 100 along the width direction or along the length direction based on the size and shape of the tooth socket 12 or wound to be treated. That is, a width of the rolled up foldable absorbent apparatus 100 may correspond to a width of the tooth socket 12. The rolled up foldable absorbent apparatus includes a first portion 100a, a second portion 100b, and a third portion 100c. The first and third portion 100a and 100c are configured to apply a pressure to the user's gums 14 so that the second portion 100b can apply and maintain a constant pressure against the tooth socket 12.

That is, the rolled up foldable absorbent apparatus 100 may then be wrapped over the tooth socket 12 such that the second portion 100b of the foldable absorbent apparatus 100 is held within and against the tooth socket 12 by pressing the first and third portions 100a, 100c against the user's gums 14 and/or jaw bone 16 adjacent or on either side of the tooth socket 12.

The malleable material layer 106 enclosed within the first and second absorbent pad layers 102, 104 allows the foldable absorbent apparatus 100 to be rolled or formed in various shapes and maintains the formed shape. The first and third portions 100a, 100c of the foldable absorbent apparatus 100 may be compressed against the user's gums by applying a pressure on the foldable absorbent apparatus 100 and forcing the first and third portions 100a, 100c against sides of the user's gums 14. The first and third portions 100a, 100c of the foldable absorbent apparatus 100 remain in the formed position so that the second portion 100b of the foldable absorbent apparatus 100 may apply a constant pressure to the tooth socket 12, while at the same time the first and second absorbent pad layers 102, 104 absorb blood and/or any other fluids from the sooth socket 12 to help stop bleeding and to promote healing of the tooth socket 12.

From the foregoing description, it will be recognized by those skilled in the art that a foldable absorbent apparatus that provides a constant amount of pressure to a tooth socket or other wound while at the same time absorbing blood and other fluids has been provided. The foldable absorbent apparatus according to the present general inventive concept may be used to stop the bleeding of the user's tooth socket without requiring a medical professional or the user to hold the foldable absorbent apparatus in place. As a result, the amount of time the medical professional is required remain with the user merely to assist in providing constant pressure to the tooth socket is substantially reduced.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A foldable absorbent apparatus to ameliorate bleeding of a wound, the foldable absorbent apparatus comprising:
   a first and second absorbent pad layer to absorb a fluid;
   a medication layer disposed between the first and second absorbent layers; and
   a malleable material layer enclosed within the first and second absorbent layer configured to be formed in various shapes,
   wherein the malleable material allows the first and second absorbent pad layers to be formed in various shapes to apply and maintain a positive pressure to a wound while at the same time absorbing fluids from the wound to promote healing of the wound.

2. The apparatus of claim 1, further comprising a time-release layer disposed between the first absorbent layer and the medication layer to control a time the medication layer reaches the first absorbent layer.

3. The apparatus of claim 1, wherein the medication layer includes at least one of a pain medication, a coagulant, an antibiotic, and an anti-bacterial agent.

4. The apparatus of claim 1, wherein the first and second absorbent layer is formed of at least one material selected from a group consisting of cotton, gauze, and a polymer material.

5. The apparatus of claim 4, wherein the polymer material is formed of at least one material selected from a group consisting of polyacrylate, chitosan, polyamine, polylysine, polyethylene, xanthan, a cellulosic polymer, a dextran, a starch, or any combinations thereof.

6. The apparatus of claim 1, further comprising a friction member disposed on an outer surface of at least one of the first absorbent layer and the second absorbent layer.

7. The foldable absorbent apparatus of claim 1, wherein at least one of the first and second absorbent pad layers is in direct contact with the wound.

8. The foldable absorbent apparatus of claim 1, wherein the malleable material layer comprises at least one of a metal, a polymer, an alloy, a fiber, foil, or any other material which is malleable or formable to various shapes and is capable of retaining the shape in order to secure and hold the foldable absorbent apparatus in a desired position or shape.

9. The foldable absorbent apparatus of claim 1, as sized and configured to apply and maintain positive pressure to a wound resulting from a dental procedure.

\* \* \* \* \*